United States Patent
Suzuki

(10) Patent No.: US 8,162,823 B2
(45) Date of Patent: Apr. 24, 2012

(54) ENDOSCOPE APPARATUS

(75) Inventor: Takashi Suzuki, Chofu (JP)

(73) Assignee: Olympus Corporation, Tokyo (JP)

( * ) Notice: Subject to any disclaimer, the term of this patent is extended or adjusted under 35 U.S.C. 154(b) by 1074 days.

(21) Appl. No.: 12/037,498

(22) Filed: Feb. 26, 2008

(65) Prior Publication Data

US 2009/0147251 A1  Jun. 11, 2009

(30) Foreign Application Priority Data

Feb. 28, 2007 (JP) ................. 2007-050632

(51) Int. Cl.
*A61B 1/04* (2006.01)
*A61B 1/00* (2006.01)

(52) U.S. Cl. .................. 600/132; 600/102; 600/131
(58) Field of Classification Search .................. 600/101, 600/102, 132, 104, 120, 131
See application file for complete search history.

(56) References Cited

U.S. PATENT DOCUMENTS

| 5,627,584 | A  | * | 5/1997 | Nishikori et al. ............... 348/72 |
| 6,846,285 | B2 | * | 1/2005 | Hasegawa et al. ............ 600/102 |
| 7,108,656 | B2 | * | 9/2006 | Fujikawa et al. ............. 600/102 |
| 7,502,224 | B2 | * | 3/2009 | Motoe ...................... 361/679.33 |
| 2002/0043608 | A1 | * | 4/2002 | Nakata et al. ................. 248/560 |

FOREIGN PATENT DOCUMENTS

| JP | 10-057299 A | 3/1998 |
| JP | 2003-244505 A | 8/2003 |
| JP | 2004-081797 | 3/2004 |

* cited by examiner

*Primary Examiner* — Thomas J Sweet
*Assistant Examiner* — Alireza Nia
(74) *Attorney, Agent, or Firm* — Scully, Scott, Murphy & Presser, P.C.

(57) ABSTRACT

An endoscope apparatus according to the present invention includes an apparatus main body having a protector which is provided so as to project from the outer surface of a box-shaped housing, and an endoscope unit including a connector portion detachably attached to the housing, thereby reducing a shock applied to the housing and preventing damage of the housing.

12 Claims, 13 Drawing Sheets

ENDOSCOPE APPARATUS

This application claims benefit of Japanese Application No. 2007-50632 filed on Feb. 28, 2007, the contents of which are incorporated by this reference.

BACKGROUND OF THE INVENTION

1. Field of the Invention

The present invention relates to an endoscope apparatus including an apparatus main body to which an endoscope is connected in a freely attachable and detachable manner.

2. Description of the Related Art

As is well known, endoscope apparatuses have been widely used in medical fields and industrial fields. An endoscope apparatus used in a medical field is capable of observing an organ in a body cavity by inserting a thin and long insertion portion of the endoscope into the body cavity, and further performing various medical treatment by using a treatment tool inserted into an insertion channel for the treatment tool, as required.

Further, an endoscope apparatus used in an industrial field is capable of performing observation of damage, corrosion, and the like, in parts to be inspected, or performing various treatment by inserting a thin and long insertion portion of the endoscope into the inside of a jet engine, a pipe in a plant and the like.

An industrial endoscope apparatus is generally configured, for example, of an endoscope which has, at the distal end portion thereof, a thin and long insertion portion provided with an image pickup unit having an image pickup lens and an image pickup device such as a CCD, and an apparatus main body to which the endoscope is connected. Note that there is also known a small endoscope apparatus in which a light source, such as an LED, is provided at the distal end of an insertion portion.

Further, in the apparatus main body, there are provided various members for driving the endoscope, such as specifically, an electric circuit which drives the image pickup unit and the light source, an image processing unit which performs processing of an picked up image signal outputted from the image pickup unit, a recording medium which records image data processed by the image processing unit, and a battery which supplies electric power to the endoscope and the apparatus main body.

As the above described industrial endoscope apparatus, for example, there is described, in Japanese Patent Application Laid-Open Publication No. 2004-81797, an endoscope apparatus having a monitor which is rotatably provided in the apparatus main body, and displays an endoscopic image picked up by the endoscope. In the endoscope apparatus as described in Japanese Patent Application Laid-Open Publication No. 2004-81797, the monitor is fixed to a fixing screw provided with a hinge of the apparatus main body, so that the monitor can be adjusted to a predetermined tilting angle with respect to the apparatus main body. Further, there is disclosed, in Japanese Patent Application Laid-Open Publication No. 2004-81797, a configuration in which the monitor can be adjusted to a predetermined tilting angle with respect to the apparatus main body by providing hinges at both side surface portions of the monitor.

SUMMARY OF THE INVENTION

An endoscope apparatus according to the present invention is featured by including: an apparatus main body having a protector which is provided so as to project from the outer surface of a box-shaped housing; and an endoscope unit having a connector portion which can be detachably attached to the housing.

The above and other objects, features and advantages of the invention will become more clearly understood from the following description referring to the accompanying drawings.

DETAILED DESCRIPTION OF THE PREFERRED EMBODIMENTS

In the following, an embodiment according to the present invention will be described with reference to the accompanying drawings. Note that an endoscope apparatus according to the present embodiment will be described by taking as an example a shoulder type industrial endoscope apparatus which is excellent in portability.

Figure 1:
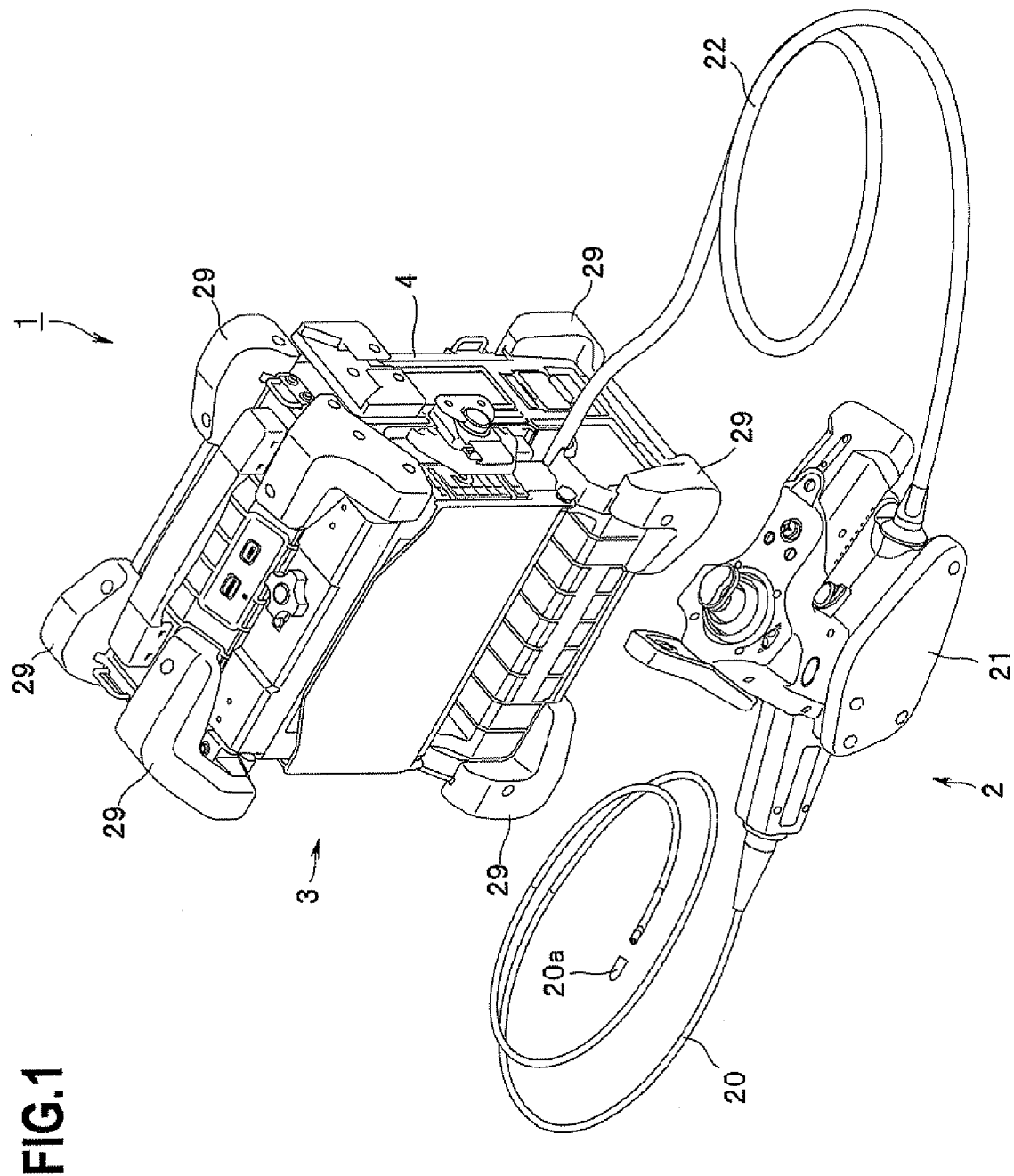
FIG. 1 is a perspective view showing an entire configuration of an endoscope apparatus according to an embodiment of the present invention.
Figure 2:
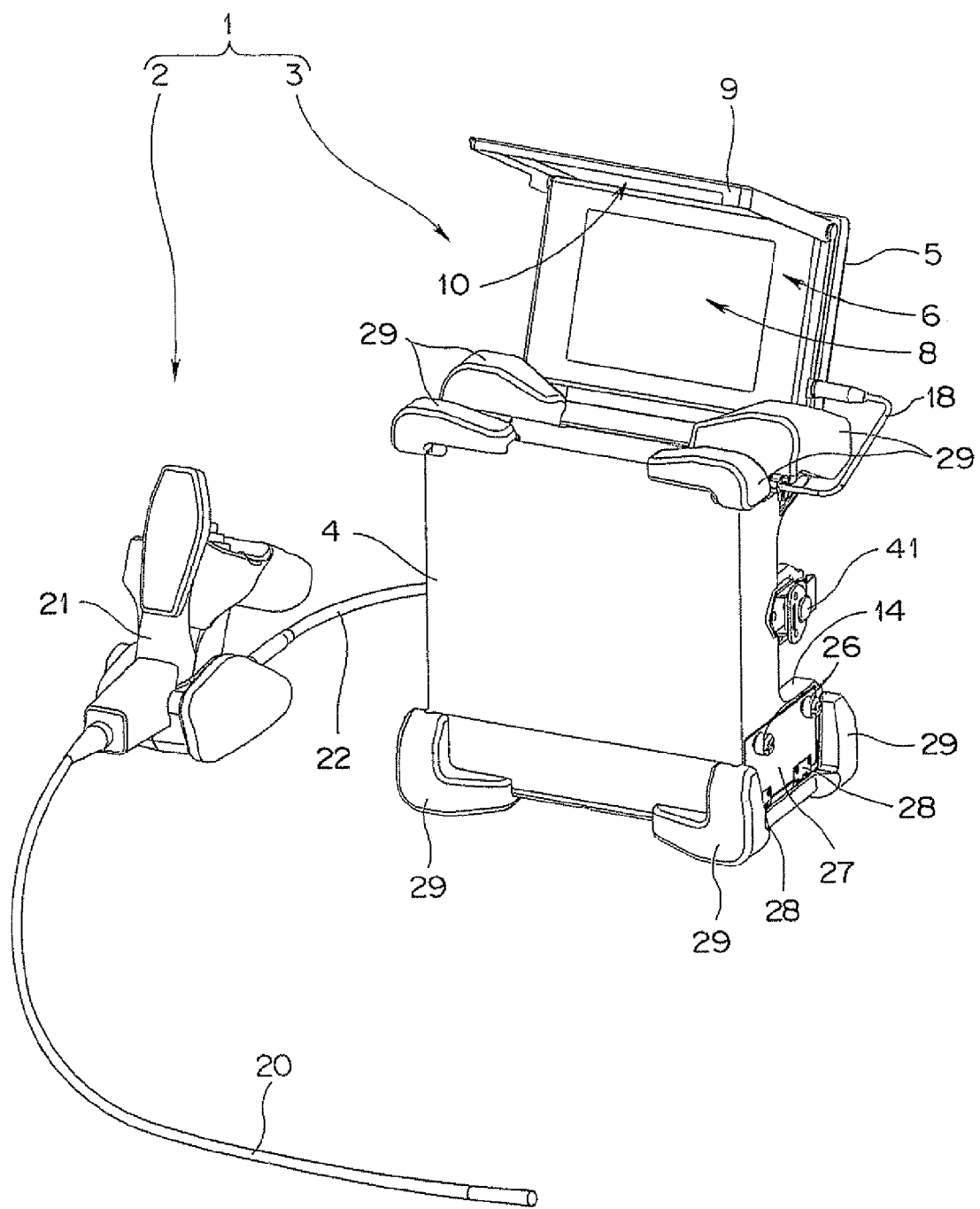
FIG. 2 is a perspective view of the endoscope apparatus in a state where a monitor is rotated and raised from an apparatus main body.
Figure 3:
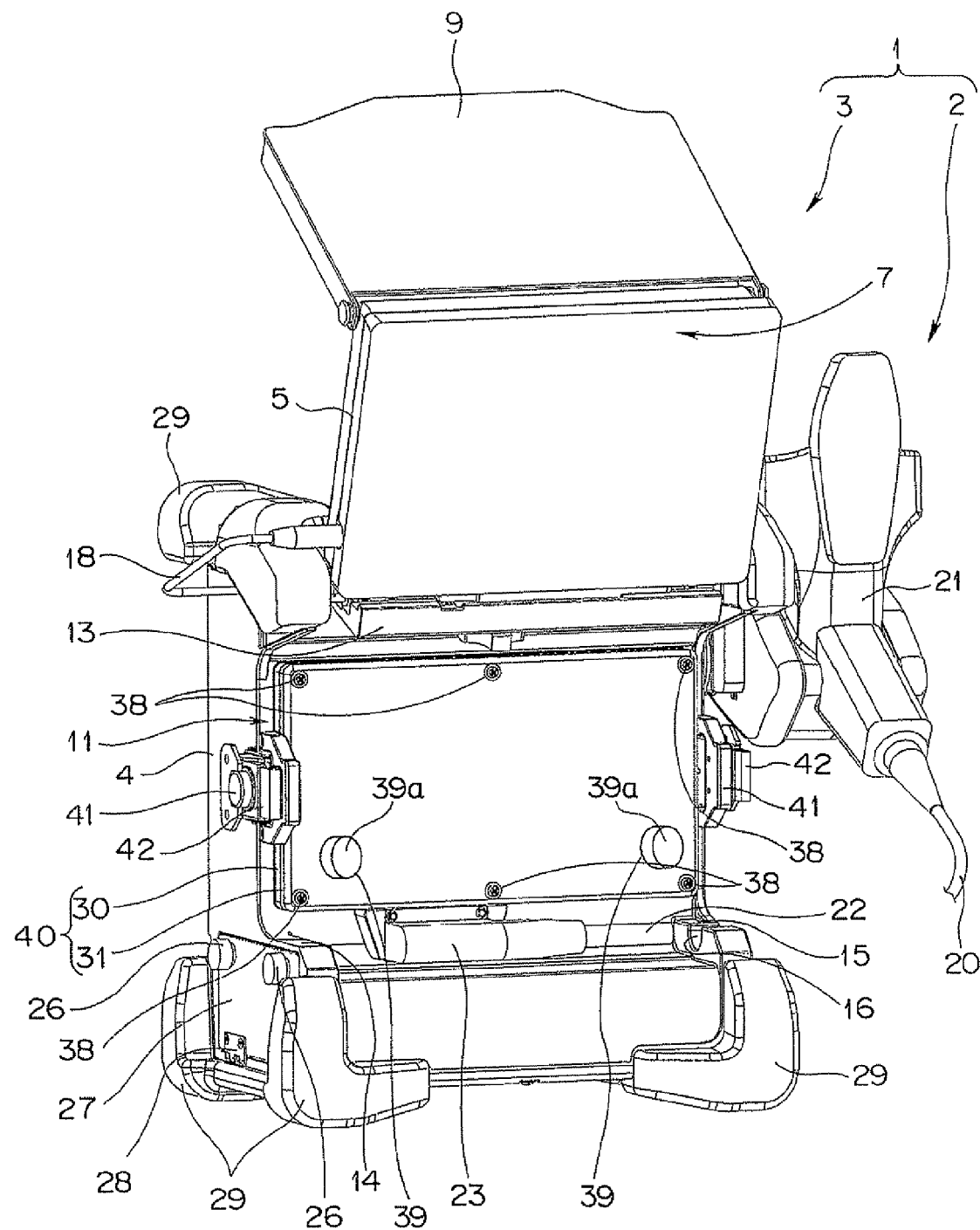
FIG. 3 is an enlarged perspective view of the endoscope apparatus when the apparatus main body is viewed from the rear face side thereof.
Figure 4:
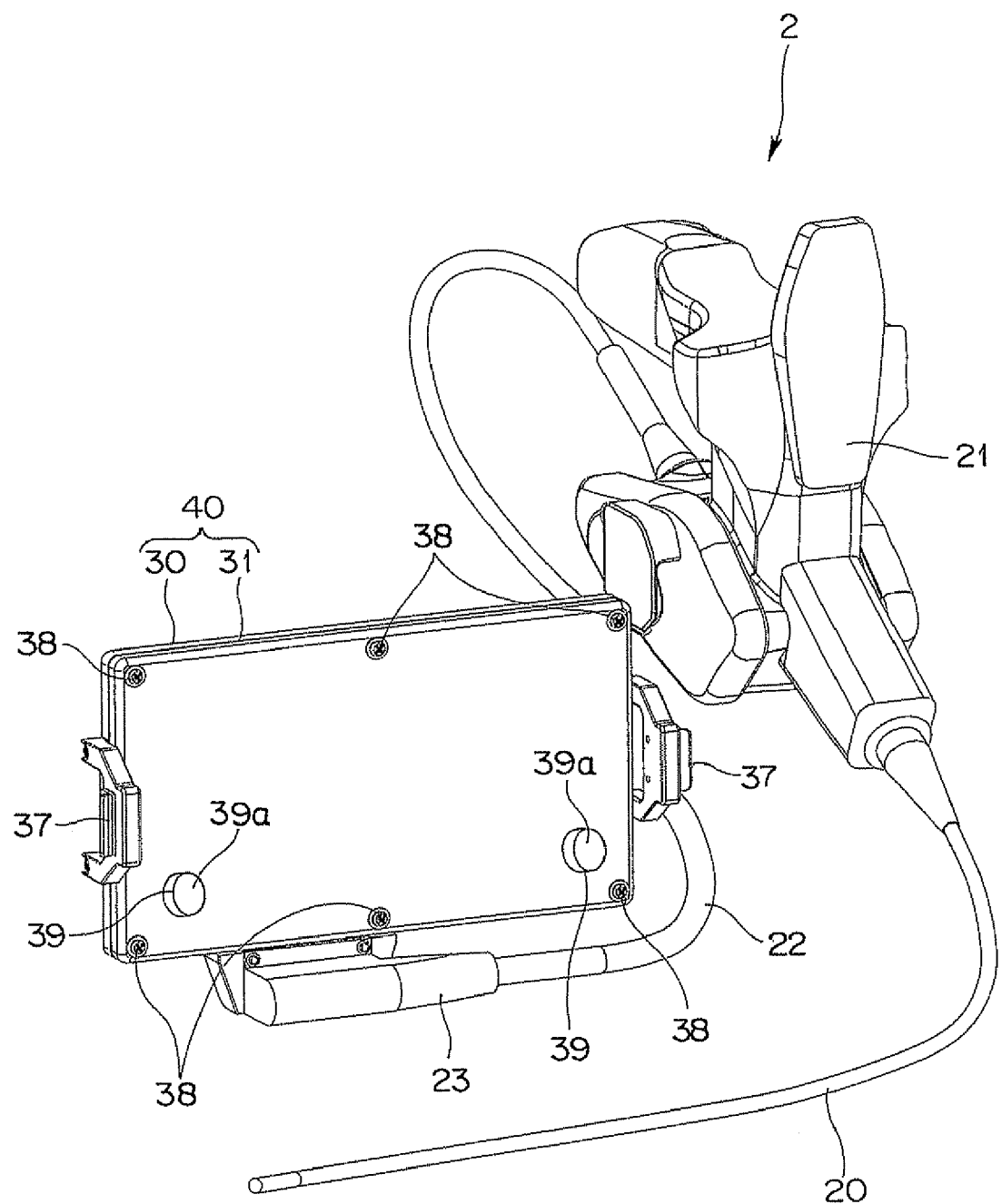
FIG. 4 is a perspective view of the endoscope, showing a state where the endoscope is removed from the apparatus main body.
Figure 5:
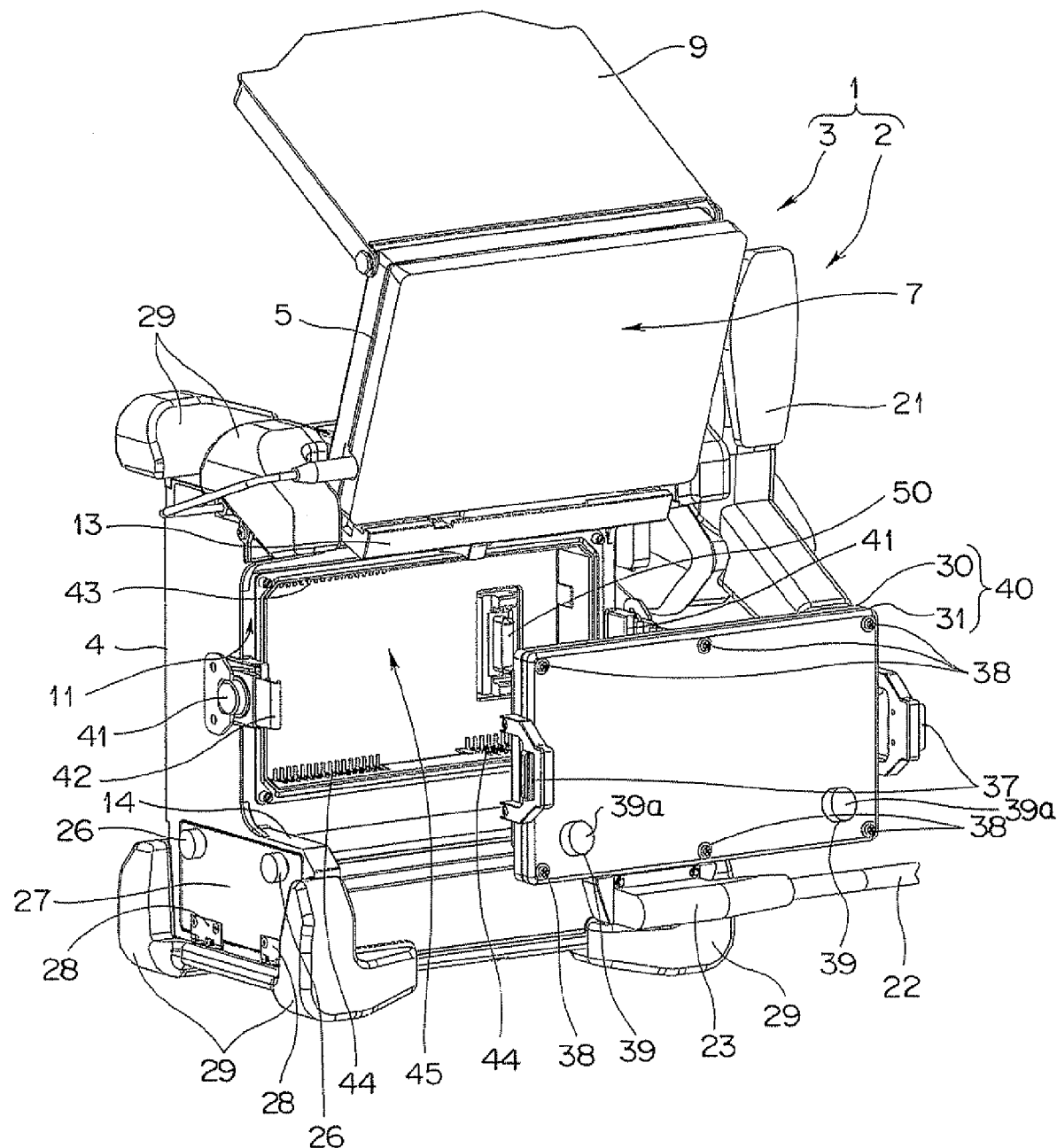
FIG. 5 is a perspective view of the endoscope apparatus, showing a state where a connector box is removed from the apparatus main body.
Figure 6:
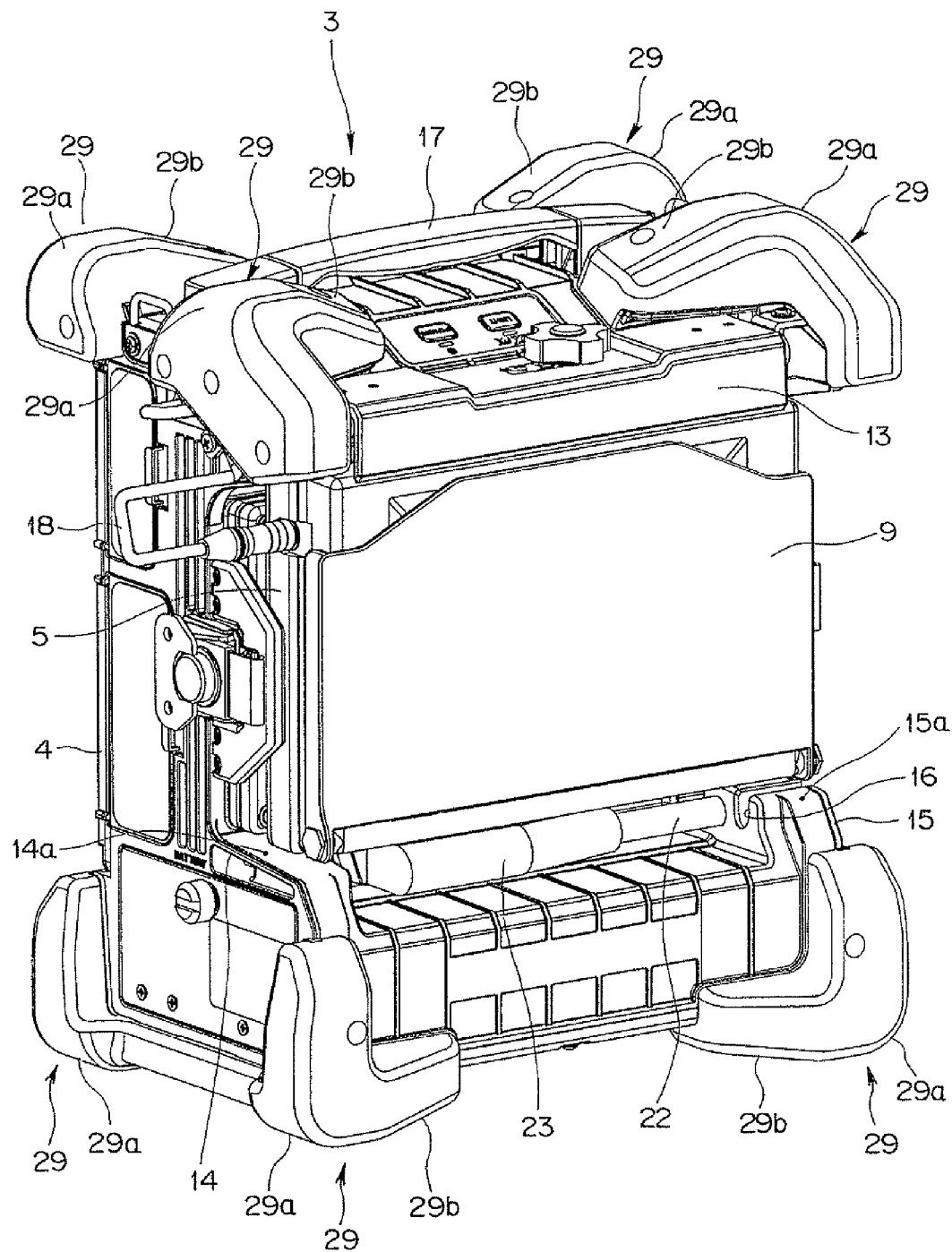
FIG. 6 is a perspective view showing the endoscope apparatus when the monitor is closed to the apparatus main body and is not used.
Figure 7:
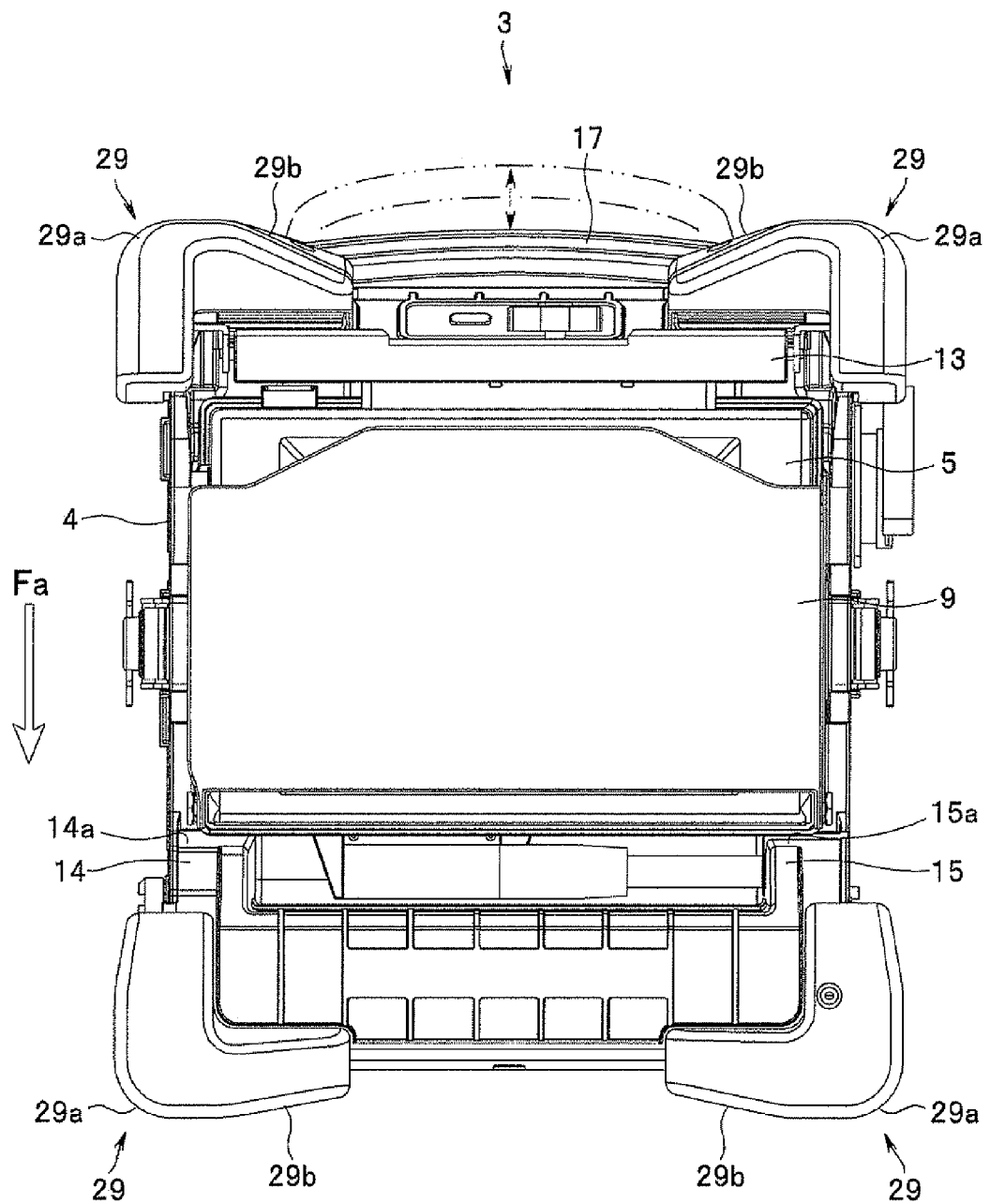
FIG. 7 is a front view of the endoscope apparatus in the state shown in FIG. 6.
Figure 8:
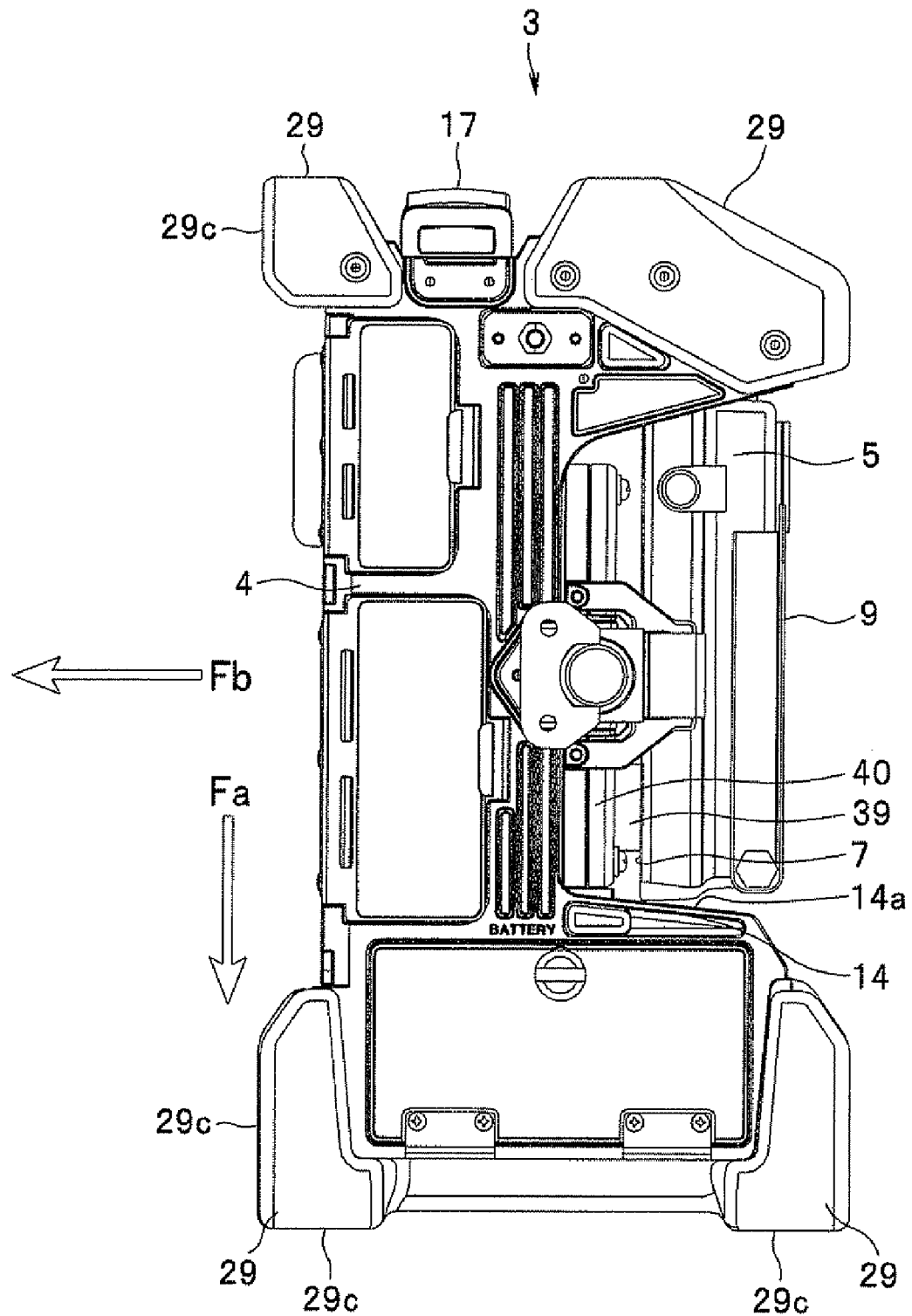
FIG. 8 is a right side view of the endoscope apparatus in the state shown in FIG. 6.
Figure 9:
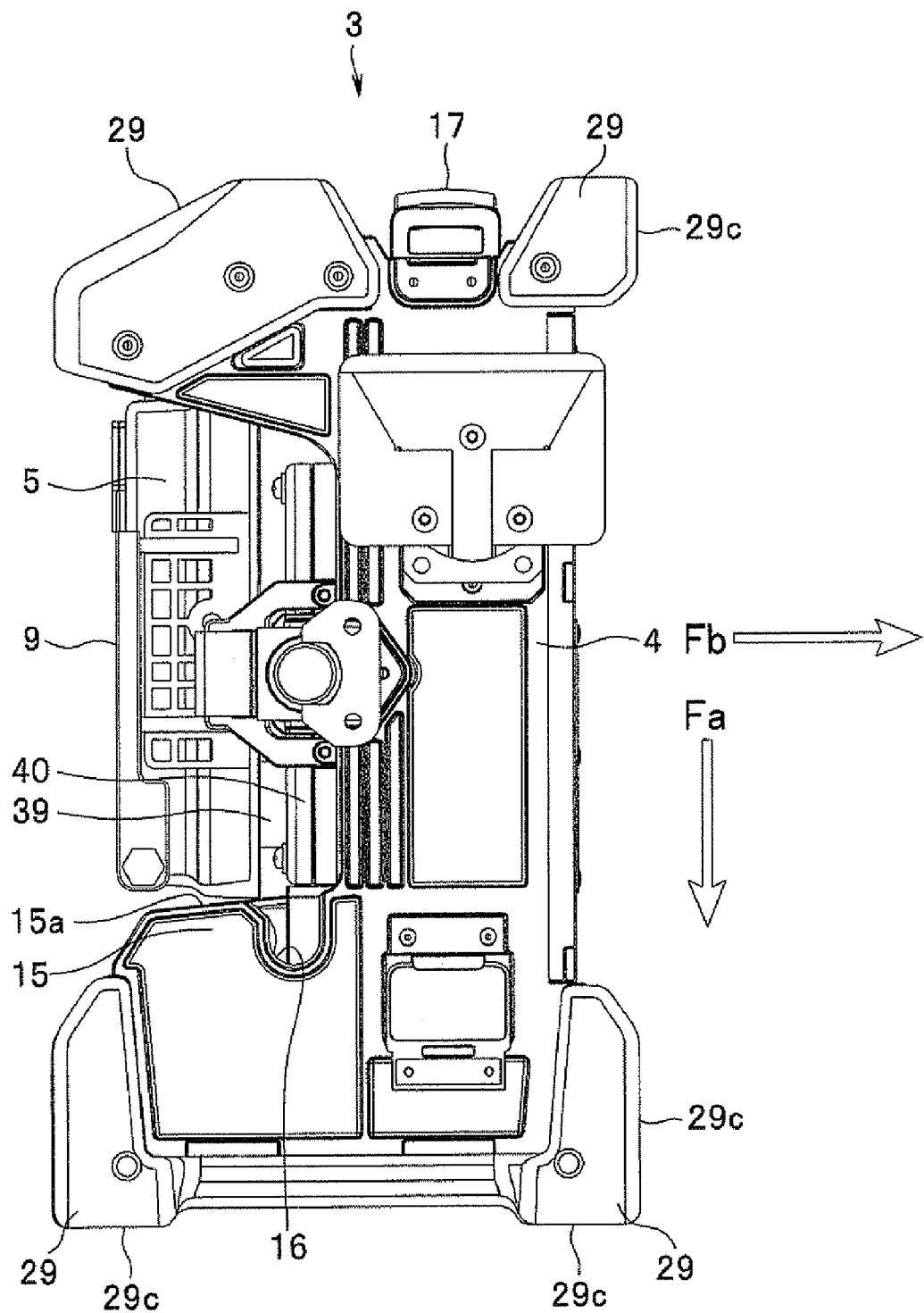
FIG. 9 is a left side view of the endoscope apparatus in the state shown in FIG. 6.
Figure 10:
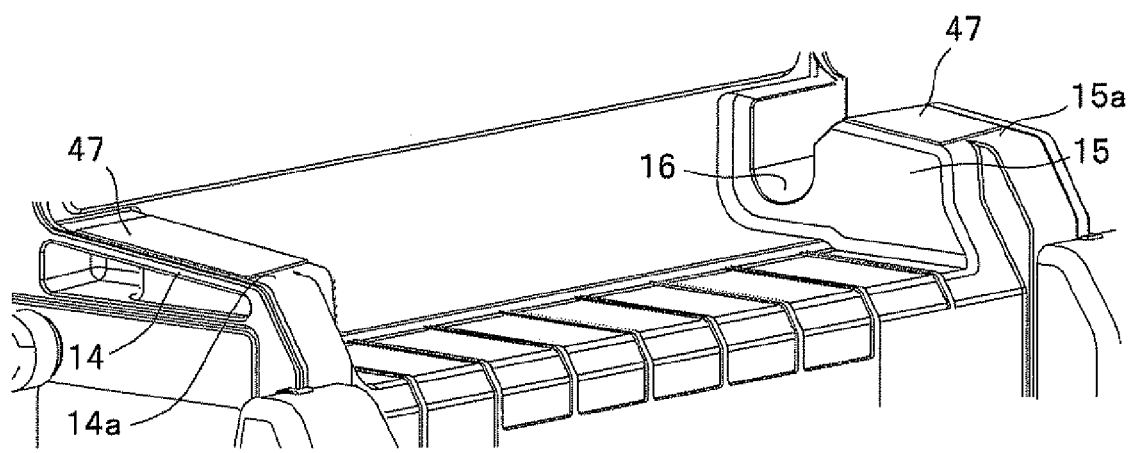
FIG. 10 is a perspective view showing a monitor shock absorbing portion as a modification.
Figure 11:
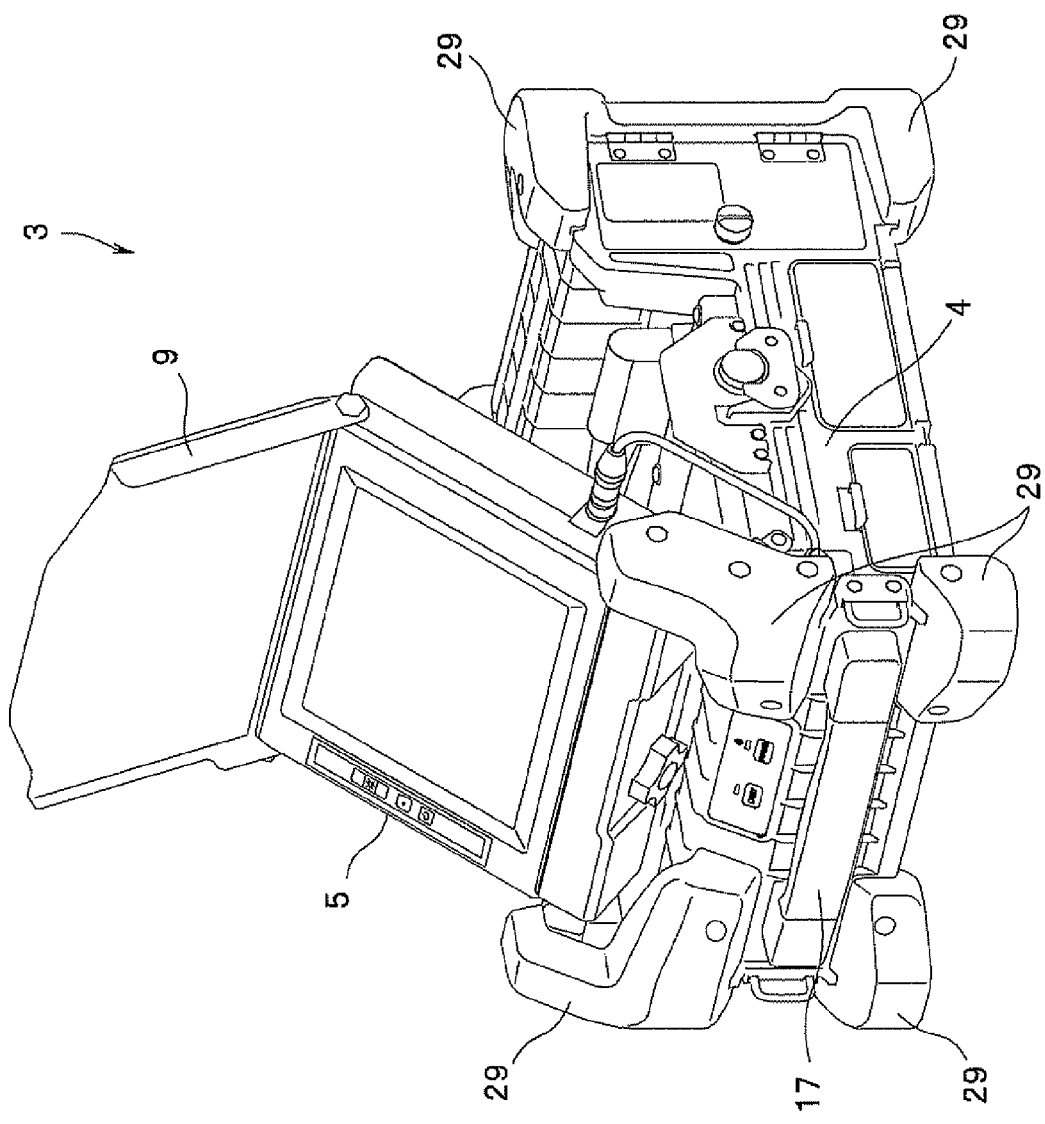
FIG. 11 is a perspective view showing a state where the apparatus main body is placed on its side when being used.
Figure 12:
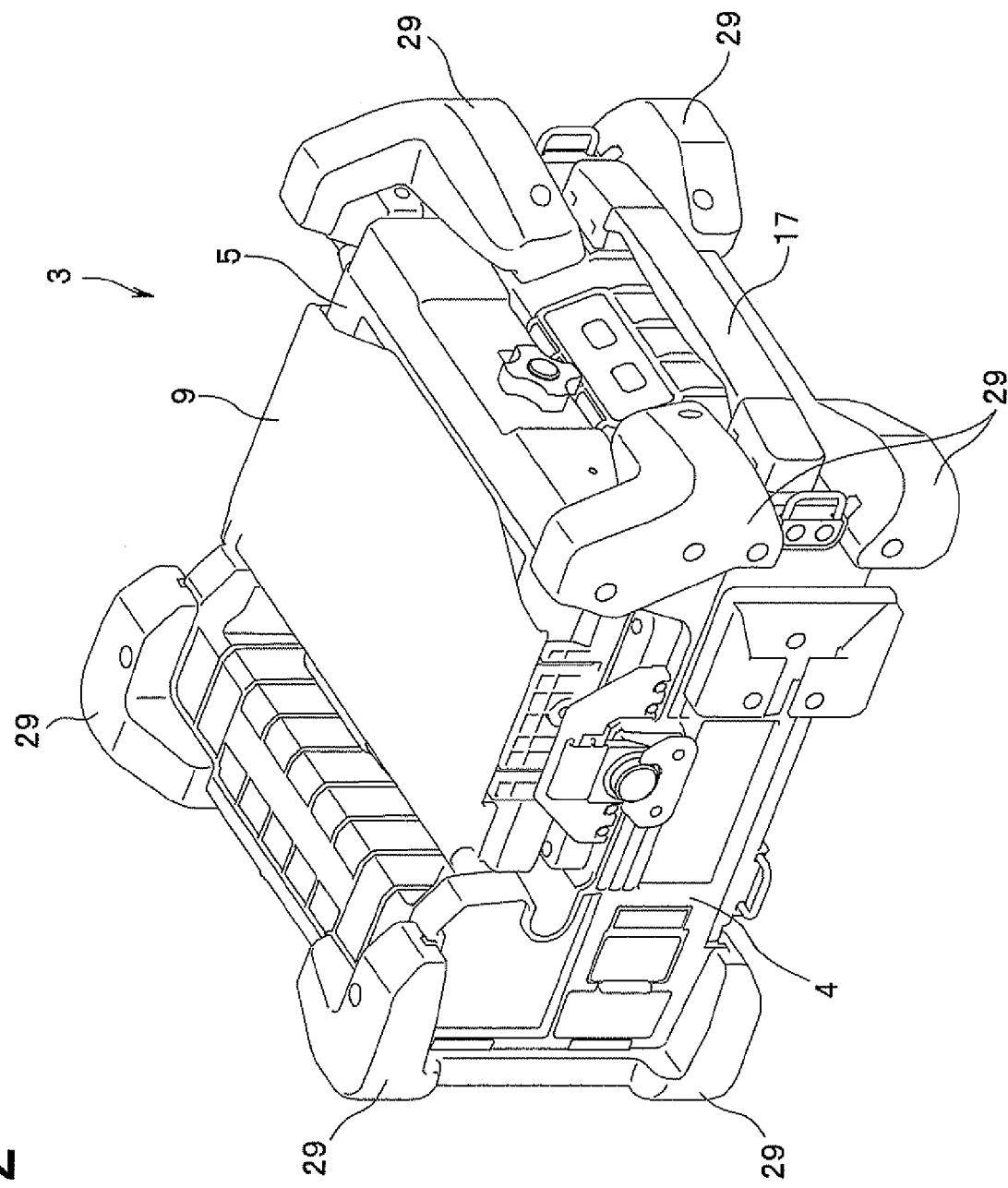
FIG. 12 is a perspective view showing a state where the apparatus main body is placed on its side when not being used.
Figure 13:
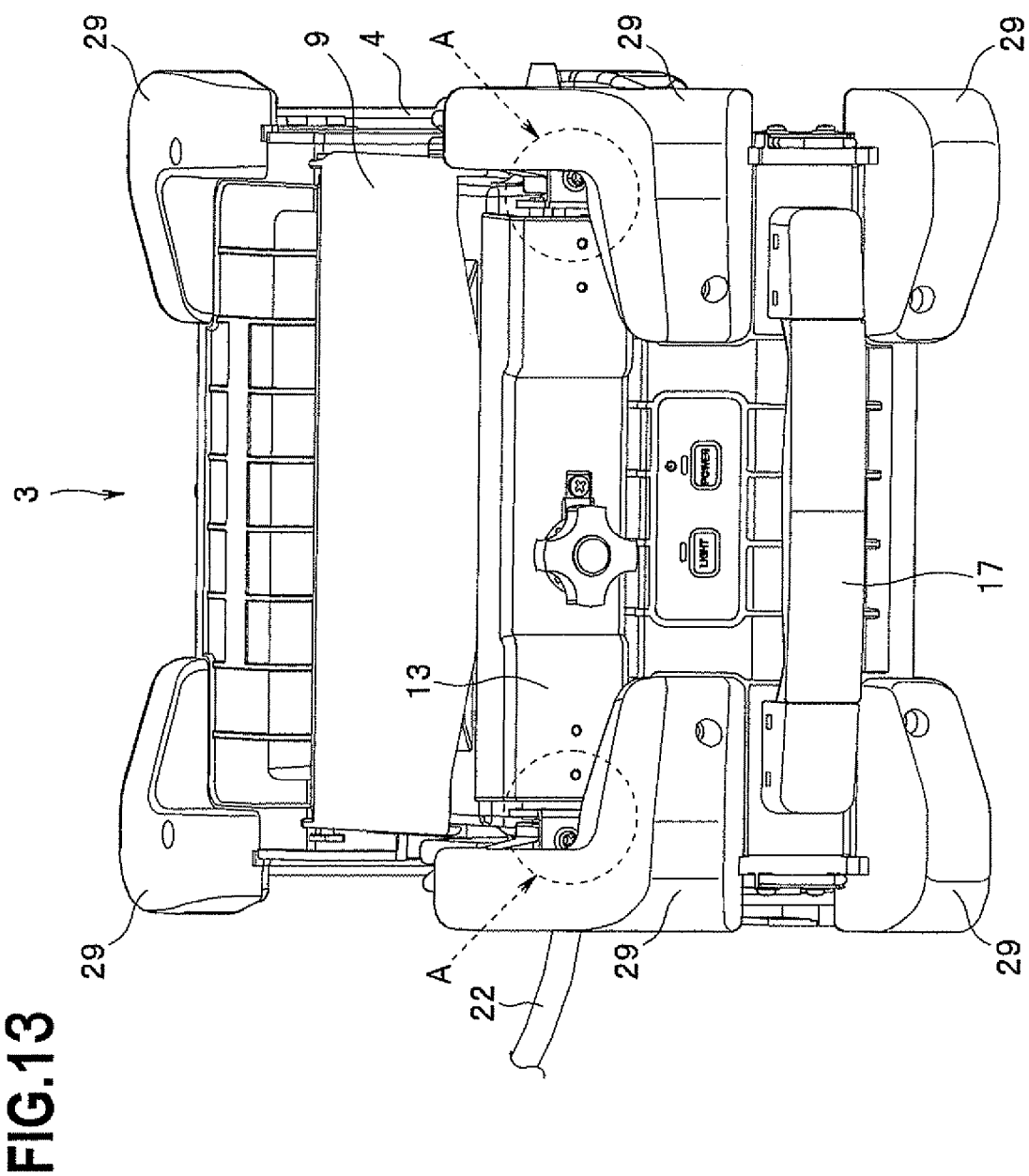
FIG. 13 is a perspective view when the apparatus main body placed on its side is viewed from the direction in which a handle portion is provided.

FIG. 1 is a perspective view showing an entire configuration of an endoscope apparatus according to an embodiment of the present invention. FIG. 2 is a perspective view in a state where a monitor is rotated and raised from an apparatus main body. FIG. 3 is an enlarged perspective view of the endoscope apparatus when the apparatus main body shown in FIG. 2 is viewed from the rear face side thereof. FIG. 4 is a perspective view of the endoscope, showing a state where the endoscope is removed from the apparatus main body shown in FIG. 3. FIG. 5 is a perspective view of the endoscope apparatus, showing a state where a connector box is removed from the apparatus main body shown in FIG. 3. FIG. 6 is a perspective view showing the endoscope apparatus when the monitor is closed to the apparatus main body and is not used. FIG. 7 is a front view of the endoscope apparatus in the state shown in FIG. 6. FIG. 8 is a right side view of the endoscope apparatus in the state shown in FIG. 6. FIG. 9 is a left side view of the endoscope apparatus in the state shown in FIG. 6. FIG. 10 is a perspective view showing a monitor shock absorbing portion as a modification. FIG. 11 is a perspective view showing a state where the apparatus main body is placed on its side when being used. FIG. 12 is a perspective view showing a state where the apparatus main body is placed on its side when not being used. FIG. 13 is a perspective view when the apparatus main body placed on its side is viewed from the direction in which a handle portion is provided.

As shown in FIG. 1 and FIG. 2, a main part of an endoscope apparatus 1 as an endoscope unit is configured of an endoscope 2, and an apparatus main body 3 to which the endoscope 2 is connected.

A main part of the endoscope 2 is configured of a thin and long flexible insertion portion 20, an operation portion 21 connected to the insertion direction proximal end side of the insertion portion 20, a universal cord 22 which is a flexible communication cable extended from the operation portion 21, and a connector box 40 (see FIG. 3 and FIG. 4) which is a connector portion, as will be described below, connected to the extended end of the universal cord 22. Note that the endoscope 2 is connected to the apparatus main body 3 by the universal cord 22 and the connector box 40.

In the inside of the distal end portion of the insertion portion 20, there is arranged an image pickup unit which has an objective optical system such as an objective lens, and an image pickup device, such as a CCD, for picking up an image of a part to be tested, and the like. A distal end adapter 20a for changing optical performance, in which there is arranged a light source, such as an LED, for illuminating the part to be tested (both not shown), or the like, is detachably mounted to the distal end portion of the insertion portion 20. Note that the image pickup unit or the light source may be provided in the inside of the operation portion 21 or in the inside covered by an exterior housing 4 of the apparatus main body 3 (hereinafter referred to as the inside of the apparatus main body 3).

In the apparatus main body 3, a monitor 5 having an image display portion 8, such as an LCD (Liquid Crystal Display) for displaying an endoscopic image picked up by the image pickup unit of the endoscope 2, is fixed to the exterior housing 4 configured as a box-shaped housing formed of a hard metal, such as magnesium.

Particularly, the monitor 5 is fixed to the outer surface of the apparatus main body 3 via a rotary supporting portion 13 (see FIG. 3). A stay configuring a rotary shaft member (not shown) is provided in the inside of the rotary supporting portion 13, and the monitor 5 is rotatably supported by the stay. More particularly, for effecting the connection between the stay and the monitor 5, a frame body of the monitor 5, in which the image display portion 8 is provided, and which is formed of synthetic resin, is rotatably supported by the stay. A communication cable 18 extended from the apparatus main body 3 is connected to the monitor 5 in a freely attachable and detachable manner. Note that the image signal subjected to photoelectric conversion by the image pickup unit of the endoscope 2 is outputted to the monitor 5 via the communication cable 18.

Further, when the endoscope 1 is used, the monitor 5 is set to a raised state in such a way that a rear face portion 7 opposite a monitor face 6 in which the image display portion 8 is provided, is rotated in the direction away from the connector box 40 (see FIG. 3 and FIG. 4), which is mounted to the rear face side of the exterior housing 4 of the apparatus main body 3, and which will be described below. Note that when the endoscope apparatus 1 is not used, the monitor 5 is closed in such a way that the rear face portion 7 of the monitor 5 is rotated so as to be overlapped with the connector box 40.

When the endoscope apparatus 1 is not used, a cover plate 9 which covers and protects the image display portion 8 is fixed to the monitor face 6 of the monitor 5 (see FIG. 6). The cover plate 9 is fixed to the monitor face 6 so that an opposite face 10 of the cover plate 9, which faces the image display portion 8, is freely opened and closed with respect to the image display portion 8.

Further, a plurality of leg portions 29, that is, eight leg portions 29 in the present embodiment, are fixed to all corner portions of the exterior housing 4 of the box-shaped apparatus main body 3. The leg portions 29 configure a protector which protects the apparatus main body 3 by absorbing a shock applied to the exterior housing 4, and are also provided so as to serve as a shock absorbing member which absorbs and reduces the shock applied to the exterior housing 4, and to enable the apparatus main body 3 to be placed in a plurality of postures. Note that the detailed configuration of the leg portion 29 will be described below.

In the exterior housing 4 of the apparatus main body 3, as shown in FIG. 5, a concave connector box housing chamber 45 (hereinafter simply referred to as a housing chamber) in which the connector box 40 is housed, is provided on an outer surface 11 side of the rear face side. Note that the housing chamber 45 is formed to have an external plane shape substantially the same as that of the connector box 40.

In the housing chamber 45, there are provided a plurality of slits 44 for discharging heat in the inside of the housing chamber 45 to the inside of the apparatus main body 3 covered by the exterior housing 4, a convex electric connector 50 to which a concave connector (not shown) of the connector box 40 is electrically connected, and the like.

Further, as shown in FIG. 6, a carrying handle portion 17 which is vertically projected and retracted, is provided in one side portion (the upper side when viewed toward the paper surface) of the exterior housing 4, and the stay (not shown) provided in the rotary supporting portion 13 for rotatably holding the monitor 5 is fixed to the one side portion side. Further, on the other side portion side opposite the one side portion side on which the stay is held, the exterior housing 4 is formed integrally with two monitor shock absorbing portions 14 and 15 projecting from the surface on which the housing chamber 45 is provided.

As shown in FIG. 6 to FIG. 9, the monitor shock absorbing portions 14 and 15 are configured to project from the outer surface 11 of the exterior housing 4 so that the monitor 5 is prevented from being brought into contact with the connector box 40 in the state where the monitor 5 is rotated and closed so as to overlap with the connector box 40. The monitor shock absorbing portions 14 and 15 are respectively provided with regulating surfaces 14a and 15a which face both end portions of one surface which is the lower surface of the monitor 5 when viewed toward the paper surface.

Further, a recessed portion 16, in which the universal cord 22 of the endoscope 2 is inserted and arranged, is formed in the monitor shock absorbing portion 15. That is, the endoscope 2 is used in the state where the universal cord 22 is extended farther than the exterior housing 4 and the plurality of leg portions 29, and where the operation portion 21 connected to the extended end of the universal cord 22, and the insertion portion 20 are extended from the apparatus main body 3.

The distance (hereinafter referred to as clearance) across the gap where the regulating surfaces 14a and 15a face the above described one surface of the monitor 5 is about 1.0 mm in the present embodiment. The clearance of 1.0 mm is provided also for obtaining the accuracy at the time of manufacture, so as to prevent the influence on the rotational operation of the monitor 5. Further, the regulating surfaces 14a and 15a may be formed into a curved arcuate shape along the path of the opposite surface, which path is formed by the rotation of the monitor 5.

Note that the clearance may be set, for example, in a range of 1.0 mm to 5.0 mm according to the kind of synthetic resin which forms the frame member for holding the image display portion 8 of the monitor 5, and in correspondence with an elongation amount of the synthetic resin at the time when a predetermined load is applied to the synthetic resin.

The connector box 40 configuring the connector portion of the endoscope 2 is a substantially box-shaped member fixed to a connector 23 provided at the extended end of the universal cord 22 of the endoscope 2, as shown in FIG. 4. The main part of the connector box 40 is configured of a concave frame member 30 and a thin plate lid 31 which is freely opened and closed with respect to an opening 32 of the frame member 30.

As shown in FIG. 4, here, on the surface of the lid 31, there are provided two shock absorbing members 39 which configure the monitor shock absorbing portion. The shock absorbing members 39 have a substantially columnar shape and are formed of an elastic member, such as rubber. When the endoscope 1 is not used, and in the state where the monitor 5 is housed in the apparatus main body 3, the shock absorbing members 39 hold the monitor 5 in such a manner that a contact surface 39a configuring a regulating surface, which is an upper surface in parallel with the lid 31 facing the rear face portion 7 as the one face of the monitor 5, is made to abut to the rear face portion 7.

Further, the lid 31 is detachably attached by screwing a plurality of screws 38 to the same number of screw holes (not shown) formed in an outer peripheral edge portion 33 of the surface of the frame member 30, which surface is opposite to the connector box housing chamber 45, and thereby is freely opened and closed with respect to the frame member 30.

The connector box 40 to which the endoscope 2 is connected can be detachably attached to the housing chamber 45, as shown in FIG. 3 and FIG. 5. After the connector box 40 is mounted to the connector box housing chamber 45, claw portions 42 of two rotary fasteners 41, which are provided on the exterior housing 4, are locked with two locking portions 37 of the connector box 40, and thereby the connector box 40 is fixed and housed in the housing chamber 45.

In the apparatus main body 3, there are provided electrical components other than the connector box 40, a recording medium which records image data subjected to image processing by an image processing substrate, a battery which supplies electric power to the endoscope 2, the apparatus main body 3, and the like.

For example, it is configured such that, as shown in FIG. 2 and FIG. 3, the battery is housed in a battery housing chamber (not shown) provided in the apparatus main body 3 so as to be removably inserted by opening and closing a battery lid 27 which is provided by a hinge 28 so as to be freely opened and closed with respect to the side surface of the exterior housing 4. Further, the battery is inserted and housed in the battery housing chamber, and then the battery lid 27 is locked by a fixing pin 26. Note that the arrangement configuration of contents in the apparatus main body 3 other than the battery is known, and hence the explanation thereof is omitted.

In the endoscope apparatus 1 according to the present embodiment configured as described above, in the state where the monitor 5 is housed in the apparatus main body 3, when a shock load is applied in the Fa and Fb directions, which are shown by the arrows in FIG. 7 to FIG. 9, one surface of the monitor 5 to which the load is applied, is brought into contact with the regulating surfaces 14a and 15a of the monitor shock absorbing portions 14 and 15, or the upper surface of the shock absorbing member 39.

More particularly, in the case where a shock load is applied in the Fa direction at the time such as when the endoscope apparatus 1 is carried, or placed on the floor, the frame member of the monitor 5, which is rotatably held by the stay of the rotary supporting portion 13, is elongated and deformed according to the material quality of the synthetic resin. At this time, the one face of the monitor 5, which faces the regulating surfaces 14a and 15a of the monitor shock absorbing portions 14 and 15, is brought into contact with the regulating surfaces 14a and 15a.

At this time, the range in which the frame member of the monitor can be elongated and deformed is limited by the clearance between the above described one face of the monitor 5 and the regulating surfaces 14a and 15a, which clearance is here set to 1.0 mm. This prevents the separation of the frame member rotatably held by the stay of the rotary supporting portion 13. As a result, in the endoscope apparatus 1 according to the present embodiment, it is possible to prevent the monitor 5 from being detached from the apparatus main body 3.

Further, when a shock load is similarly applied to the endoscope apparatus 1 in the Fb direction, as shown in FIG. 8 and FIG. 9, the shock load is absorbed by the shock absorbing member 39 which is in contact with the rear face portion 7 of the monitor 5 and provided in the connector box 40.

Note that the use arrangement condition of the endoscope 1 is mainly determined such that the arrow Fa direction or the arrow Fb direction is set to the vertically downward direction in correspondence with the arrangement positional relationship between the apparatus main body 3 and the monitor 5.

As a result, in the state where the monitor 5 is housed in the apparatus main body 3, the endoscope apparatus 1 according to the present embodiment is capable of preventing the monitor 5 from being detached from the apparatus main body 3, and reducing a damage, a failure, or the like, of the monitor 5, when a shock load is applied in the vertical direction corresponding to a plurality of installation directions, that is, the two directions in the present embodiment, under the use arrangement condition.

Note that as shown in FIG. 10, the monitor shock absorbing portions 14 and 15 may be configured such that an impact absorbing member 47, such as a film sheet and a rubber sheet, is stuck on the regulating surfaces 14a and 15a of the monitor shock absorbing portions 14 and 15. The monitor shock absorbing portions 14 and 15, to which the impact absorbing member 47 is stuck, are thereby prevented from being damaged due to the contact with the one surface of the monitor 5, and from being rusted due to the coating separation. Of course, the shock that the monitor 5 receives when being brought into contact with the monitor shock absorbing portions 14 and 15, is reduced by the shock absorbing member 47.

Note that in the present embodiment, two monitor shock absorbing portions 14 and 15 are provided integrally with the exterior housing 4, but the present invention is not limited to this. The monitor shock absorbing portions may be provided separately from the exterior housing 4 or only one shock absorbing portion may of course be provided as long as the one shock absorbing portion has a regulating surface facing the above described one surface of the monitor 5. Further, the monitor shock absorbing portion may be provided with an extensive regulating surface which faces the one surface of the monitor 5, and which is configured such that the respective regulating surfaces 14a and 15a of the monitor shock absorbing portions 14 and 15 according to the present embodiment are continuously formed.

Next, there will be described in detail the configuration of the plurality of leg portions 29 which serve as the protector and are arranged so as to cover the corner portions of the exterior housing 4 of the endoscope apparatus 1.

As shown in FIG. 6 to FIG. 9, the plurality of leg portions 29, eight leg portions 29 in the present embodiment, are provided for placing the apparatus main body 3 as described above, and are formed in a block shape by, for example, rubber including elastic members such as NBR (nitrile butane rubber), alpha gel, resin, or a foamed member. Further, the leg portions 29 are formed into a substantially L-shape when viewed from one direction, and are provided so as to project from all the outer surfaces of the exterior housing 4.

The leg portions 29 configure a shock absorbing member, and absorb a shock load which is applied to the exterior housing 4 when the apparatus main body 3 is mounted, or when the apparatus main body 3 is accidentally dropped. Further, the leg portions 29 are provided to project from the outer surface of the exterior housing 4, so as to be able to protect the exterior housing 4 by preventing the exterior housing 4 from being brought into contact with the other article and being damaged.

Further, the leg portions 29 have a curved surface portion 29a whose outer shape portion covering the corner portion of the exterior housing 4 is formed in an arcuate shape, as shown in FIG. 6 and FIG. 7. That is, the curved surface portion 29a formed in the leg portions 29 is capable of protecting the exterior housing 4 by effectively distributing the shock load applied to the direction of the corner portion of the exterior housing 4.

Note that the leg portions 29 facing each other respectively have, in the mutually facing direction, inclined portions 29b inclined to the surface side of the exterior housing 4. When the user places the apparatus main body 3, in particular, on an irregular floor surface, on an equipment in a plant, or the like, the user is able to place the apparatus main body 3 in a stable state by avoiding the recessions and projections of the installation place with the inclined portions 29b of the leg portions 29. Further, the inclined portion 29b is formed in each of the four leg portions 29 on the upper side on which the handle portion 17 is provided. Thus, when grasping the handle portion 17, the user is not disturbed by the leg portions 29, and is able to smoothly grasp the handle portion 17.

Meanwhile, the endoscope apparatus 1 according to the present embodiment is configured to enable the apparatus main body 3 to be placed in a plurality of postures. Specifically, the placed postures of the apparatus main body 3 of the endoscope apparatus 1 include a posture at the time when the monitor 5 is raised from the exterior housing 4 and is used, as shown in FIG. 2, FIG. 3 or FIG. 11, a posture at the time when the monitor 5 is housed in the exterior housing 4 and is not used, as shown in FIG. 1, FIG. 6 to FIG. 9 or FIG. 12, and the like. That is, the apparatus main body 3 can be placed in a plurality of postures, here two postures, such as the state of vertical disposition in which the handle portion 17 is positioned on the upper side, as shown in FIG. 1 to FIG. 3, and FIG. 6 to FIG. 9, and the state of horizontal disposition in which the handle portion 17 is positioned on the lateral side, as shown in FIG. 11 and FIG. 12.

Further, as shown in FIG. 8 and FIG. 9, each of some of the plurality of leg portions 29 of the apparatus main body 3 has a planar installation surface 29c in the surface separated outward from and in parallel with the outer surface of the exterior housing 4, and in a portion which is brought into contact with the floor surface, or the like, when the apparatus main body 3 is installed. Note that in the present embodiment when viewed toward the paper surface in FIG. 8 and FIG. 9, the leg portion 29 in contact with the lower surface of the exterior housing 4 and with the rear face opposite the housing side of the monitor 5, have the planar installation surface 29c in a surface separated outward from and in parallel with the outer surface of the exterior housing 4, which outer surface is the lower surface or the rear face. That is, the apparatus main body 3 is configured such that the installation surface 29c of the leg portion 29 is first brought into contact with the floor surface, or the like, and hence the apparatus main body 3 is selectively placed in mainly the two postures without the exterior housing 4 being brought into contact with the floor surface, or the like.

Further, the four leg portions 29 provided to project from the outer surface 11 of the exterior housing 4, in which the connector box housing chamber 45 is formed, are arranged so as to project from the outer surface of the connector box 40 (see FIG. 3, FIG. 8 and FIG. 9) which is mounted to the connector box housing chamber 45 and configures the connector portion of the endoscope 2. Thereby, in the state where the connector box 40 is mounted to the connector box housing chamber 45 of the exterior housing 4, the connector box 40 is protected in such a manner that the four leg portions 29 absorb a shock applied at the time when the apparatus main body 3 is placed, or the like, and prevent the connector box 40 from being brought into direct contact with the other articles and being damaged.

Further, the four leg portions 29 are provided so as to project from the outer surface of the monitor 5, also in the state where the monitor 5 is housed in the exterior housing 4 (see FIG. 8 and FIG. 9). Thereby, in the state where the monitor 5 is housed in the exterior housing 4, the monitor 5 is protected in such a manner that the four leg portions 29 absorb a shock applied at the time when the apparatus main body 3 is placed, or the like, and prevent the monitor 5 from being brought into direct contact with the other articles and being damaged.

Note that the two leg portions 29 provided on the one surface side of the exterior housing 4, on which the handle portion 17 is provided, and provided on the side of the rotary supporting portion 13 which rotatably supports the monitor 5, are respectively provided to project so as to cover a part of the both ends of the rotary supporting portion 13 (the part shown by the broken line circle A in FIG. 13). That is, the two leg portions 29 cover the part of the both ends of the rotary supporting portion 13 which rotatably supports the monitor 5 with respect to the exterior housing 4, and respectively protect the both end portions of the stay (not shown) which is provided in the rotary supporting portion 13 and serves as the rotary shaft of the monitor 5. Thereby, at the time of placing the apparatus main body 3, or the like, the two leg portions 29 reduce the shock load to the stay which rotatably holds the monitor 5, and reduce the load applied to the stay. Further, the two leg portions 29 are arranged so as not to interfere with monitor 5 and not to hinder the rotation of the monitor 5.

Further, the four leg portions 29 provided on the one surface side of the exterior housing 4, on which the handle portion 17 is provided so as to be vertically projected and retracted, are provided so as to project from the handle portion 17 (see FIG. 7), in the state where the handle portion 17 is moved to the lower side (the state where the handle portion 17 is not extracted). Thereby, in the state where the handle portion 17 is retracted to the side of the exterior housing 4, the handle portion 17 is also protected in such a manner that the four leg portions 29 prevent the handle portion 17 from being brought into direct contact with the other articles and being damaged.

As described above, the endoscope apparatus 1 according to the present embodiment is configured such that the plurality of leg portions 29, serving as a protector, are provided so as to project from the exterior housing 4, in order to reduce the shock applied mainly to the exterior housing 4 in which various precise components of the apparatus main body 3 are incorporated, and to protect the various precise components of the apparatus main body 3. Further, even in the state where the connector box 40 configuring the connector portion of the endoscope 2 is connected to the exterior housing 4, and where the monitor 5 is housed in the exterior housing 4, the plurality of leg portions 29 are provided so as to project from the connector boxes 40 and the monitor 5, and thereby are capable of reducing the shock applied to the connector box 40 and the monitor, and protecting the connector box 40 and the monitor.

The present invention described in the above embodiment is not limited to the above described embodiment and modifications, and various modifications are possible in an implementation stage within the scope and spirit of the present invention. Further, various stages of the present invention are included in the above described embodiment, and various inventions may be extracted by properly combining the plurality of disclosed constitution elements.

For example, even when several constitution elements are eliminated from all the constitution elements as shown in the embodiment, so long as it is possible to solve the above described problem and an effect as described as the effect of the present invention is obtained, the configuration in which the constitution elements are eliminated may also be extracted as the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
   an apparatus main body including a box-shaped housing;
   a monitor which is fixed rotatably with respect to an outer surface of the apparatus main body and housed in the apparatus main body by a rotational operation of the monitor;
   an endoscope unit including a connector portion positioned on a rear face portion side of the monitor housed in the housing and detachably attached to the housing; and
   a protector provided on at least both end surfaces of a rotary supporting portion of the monitor, projected from an outer surface of the housing and fixed so as to cover a corner portion of the housing.

2. The endoscope apparatus according to claim 1, wherein a portion of the protector, which covers the housing, has a curved surface portion formed in an arcuate shape.

3. The endoscope apparatus according to claim 1, wherein the protector has an installation surface for installing the housing on a ground surface, and the like, in a surface which is separated outward from and in parallel with the outer surface of the housing.

4. The endoscope apparatus according to claim 1,
   wherein a plurality of the protectors are provided to the housing, and
   wherein the plurality of protectors have an inclined portion inclined to the outer surface side of the housing in a direction in which the protectors face each other.

5. The endoscope apparatus according to claim 1, wherein the protector is formed of a shock absorbing member which absorbs a shock applied to the housing.

6. The endoscope apparatus according to claim 1, wherein the protector is provided to cover a part of both ends of a rotary supporting portion which rotatably supports the monitor with respect to the housing, and to project from the rotary supporting portion, without interfering with the monitor at the time when the monitor is rotated with respect to the housing.

7. The endoscope apparatus according to claim 1, further comprising:
   a handle portion which is provided to the housing and is used for carrying the housing, the handle portion being movable in parallel to a surface of the housing in a direction separating from the housing and in a direction approaching the housing,
   wherein the protector is provided to project from a position of an outer surface side of the handle portion when the handle portion is moved in the direction approaching the housing.

8. The endoscope apparatus according to claim 1, wherein the endoscope unit includes an endoscope and a cable extended longer than the protector in a state where the connector portion is mounted to the housing by connecting the endoscope to the connector portion.

9. The endoscope apparatus according to claim 1, further comprising a shock absorbing portion provided to the housing, including a recessed portion for housing the monitor, and configured to include a regulating surface which is formed on a surface of the housing which faces a surface on a side opposite to a side where the monitor is rotatably supported and regulates the movement of the monitor, when housing the monitor.

10. The endoscope apparatus according to claim 9, wherein the shock absorbing portion is provided to project from the outer surface of the housing, which outer surface faces the rear face portion of the housed monitor.

11. The endoscope apparatus according to claim 9, wherein a shock absorbing member is provided on the regulating surface.

12. The endoscope apparatus according to claim 9, wherein the shock absorbing portion is provided at a position of the housing, which position faces the one surface of the monitor, and is separated by a predetermined distance from the one surface of the monitor, when the monitor is housed in the apparatus main body.

* * * * *